United States Patent [19]

Kowalski et al.

[11] Patent Number: 4,660,549

[45] Date of Patent: Apr. 28, 1987

[54] ADJUSTABLE HEAD SUPPORT FOR CHIROPRACTIC TABLE

[75] Inventors: Frank P. Kowalski, Des Plaines; Donald J. Westphal, Elgin, both of Ill.

[73] Assignee: Standex International, Salem, N.H.

[21] Appl. No.: 775,226

[22] Filed: Sep. 12, 1985

[51] Int. Cl.[4] .................................... A61F 5/00

[52] U.S. Cl. .................................... 128/69; 269/328

[58] Field of Search ............... 269/323, 324, 325, 328; 128/69, 70, 73

[56] References Cited

U.S. PATENT DOCUMENTS

| | | | |
|---|---|---|---|
| 1,829,918 | 11/1931 | Andrews | 269/323 |
| 2,886,029 | 5/1959 | Thompson | 128/69 |
| 3,343,531 | 9/1967 | Thompson | 128/69 |
| 3,572,835 | 3/1971 | Kees, Jr. | 269/328 |

*Primary Examiner*—Frederick R. Schmidt
*Assistant Examiner*—Judy J. Hartman
*Attorney, Agent, or Firm*—Mason, Kolehmainen, Rathburn & Wyss

[57] ABSTRACT

An adjustable head support for a chiropractic table includes a base with a platen spaced above the base and interconnected for angular displacement relative to the base about an axis longitudinally thereof. An adjustable control system is provided for selectively controlling the amount of angular displacement between the base and the platen. The axis of rotational displacement of the platen is spaced above a head cushion supported above the platen and the axis generally coincides with the spinal column or vertabrae of a patient resting on the chiropractic table.

16 Claims, 8 Drawing Figures

FIG. 4
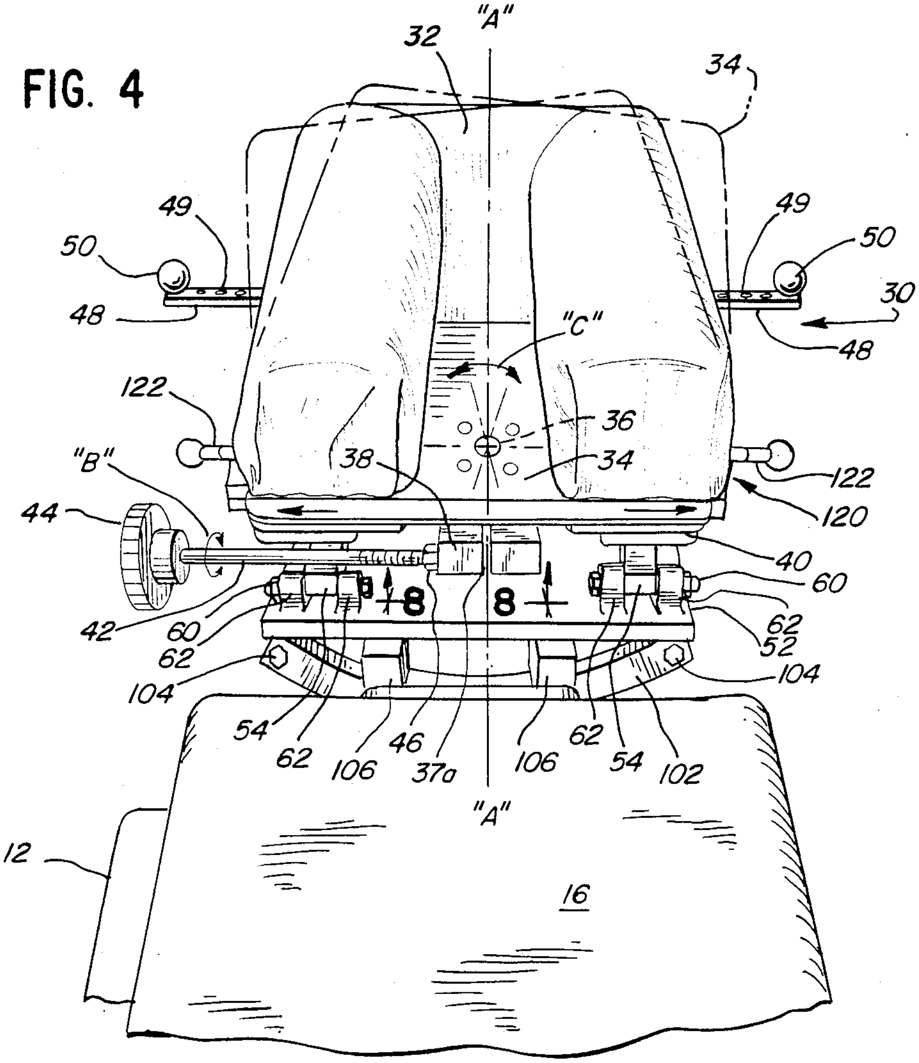
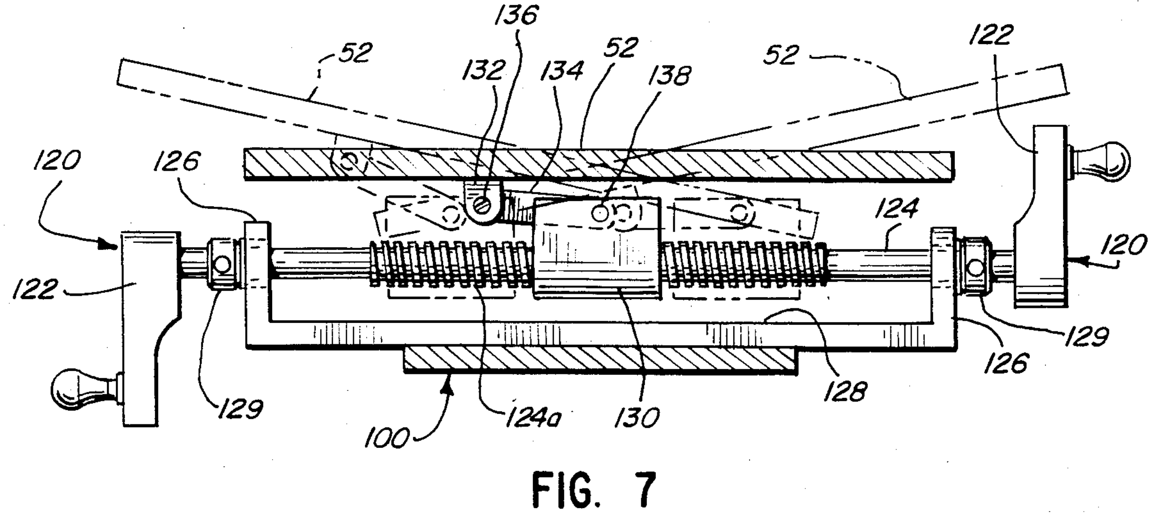
FIG. 7

ADJUSTABLE HEAD SUPPORT FOR CHIROPRACTIC TABLE

BACKGROUND OF THE INVENTION

1. Field of the Invention

The present invention relates to a new and improved adjustable head support for a chiropractic table cushion and more particularly to a head support adapted for rotational adjustment about an axis generally coextensive with the spinal column and vertabrae of the patient supported on the table. The head support apparatus also includes a cushion drop release mechanism generally similar to the chiropractic table cushion drop release mechanism disclosed in U.S. Pat. No. 4,523,581 and assigned to the same assignee as the present application.

2. Description of the Prior Art

U.S. Pat. No. 2,727,510 discloses a method for chiropractic adjustment employing a head support cushion which is adjustable relative to a table cushion supporting other portions of a patient's body. U.S. Pat. No. 2,756,744 discloses a chiropractic head rest with magnetic retaining means for use in chiropractic adjustments in the cervical region of the spine. U.S. Pat. No. 2,886,029 discloses a head rest and process of chiropractic adjustment and U.S. Pat. Nos. 2,926,660; 3,092,102; 3,343,531 and 4,230,100 disclose chiropractic tables having independently movable patient support cushions thereon for providing chiropractic adjustments on a patient.

OBJECTS OF THE INVENTION

It is an object of the present invention to provide a new and improved adjustable head support apparatus for a chiropractic table and more specifically an adjustable head support for a chiropractic table cushion permitting angular displacement of the cushion relative to an axis extending generally along the spinal axis of a patient on a table.

It is another object of the present invention to provide a new and improved chiropractic table having an adjustable head support device therein and more particularly an adjustable head support apparatus wherein angular displacement is provided for a head supporting cushion about an axis extending generally along the patient's spine.

Yet another object of the present invention is to provide a new and improved head support apparatus which includes an improved cushion drop release mechanism in addition to the aforementioned adjustable angular displacement feature.

Yet another object of the present invention is to provide a new and improved adjustable head support for a chiropractic table wherein the head support element is adjustable angularly about an axis coextensive with a patient's spinal cord and is also adjustable in terms of relative levels, spacing and angular displacement from another cushion on the table adjacent thereto.

Still another object of the present invention is to provide a new and improved adjustable head support apparatus of the character described in the preceding object additionally including a cushion drop release feature.

Still another object of the present invention is to provide an adjustable head support apparatus of the character described which is easily controlled by a doctor during patient treatment and which employs convenient indicator means for providing a visual indication of the amount of angular displacement selected.

BRIEF SUMMARY OF THE PRESENT INVENTION

The foregoing and other objects and advantages of the present invention are embodied in a new and improved adjustable head support for a chiropractic table which includes a base supported from the frame of the table and a platen spaced above the base and interconnected for angular displacement relative to the base about an axis extending longitudinally thereof and generally aligned along the spinal axis of a patient resting on the table. The adjustable head support includes an adjustment control for selectively controlling the amount of angular displacement between the platen and the base and in addition includes a cushion drop release mechanism for chiropractic adjustments of the cervical vertabrae. The novel head support also is adjustable relative to another adjacent cushion on the table in order to provide adjustment in relative height or level, angular displacement and spacing so that the wide variety of patient treatment practices may be employed.

BRIEF DESCRIPTION OF THE DRAWINGS

For better understanding of the present invention reference should be had to the following detailed description taken in conjunction with the drawings, in which:

FIG. 4 is an end elevational view of the head support apparatus;

FIG. 7 is a fragmentary, transverse cross sectional view of the head support apparatus looking in the direction of arrows 7—7 of FIG. 2.

DETAILED DESCRIPTION OF A PREFERRED EMBODIMENT

Figure 1:
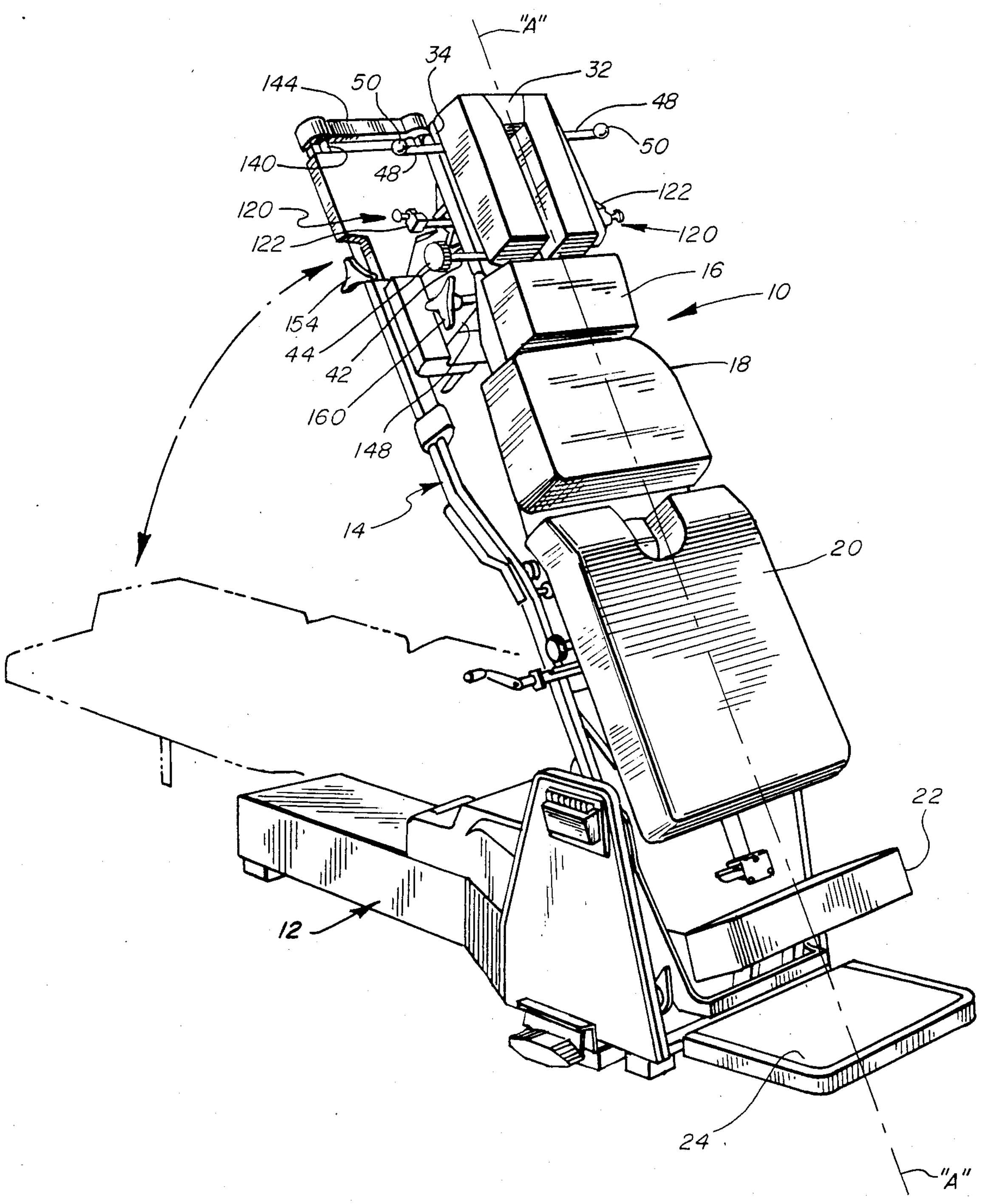
FIG. 1 is a perspective elevational view of a new and improved chiropractic patient treatment table constructed in accordance with the features of the present invention and shown in solid lines in an elevated or raised position and in phantom or dotted lines in a lower, horizontal position.

Referring now more particularly to the drawings, in FIG. 1 is illustrated a new and improved chiropractic patient treatment table constructed in accordance with the features of the present invention and referred to generally by the reference numeral 10. The patient treatment table 10 includes a lower base portion 12 adapted to rest on the floor and an upper, patient supporting frame 14 which is mounted for pivotal movement relative to the base between an upper, near vertical position as shown in solid lines in FIG. 1 and a generally horizontal, lower position as shown in dotted lines therein. The movable frame 14 provides support for a number of individually adjustable, patient supporting cushions 16, 18, 20 and 22 and a foot board 24 is provided to facilitate a patient when mounting and dismounting from the table while the table is in the upwardly extended, near vertical position as shown in solid lines in FIG. 1.

In accordance with the present invention, the table 10 includes an adjustable head support assembly 30 positioned adjacent the free (head) end of the pivotable frame 14 and the adjustable head support assembly includes a U-shaped head cushion 32 adapted to support the head and neck of an individual patient while resting on the treatment table.

Figure 2:
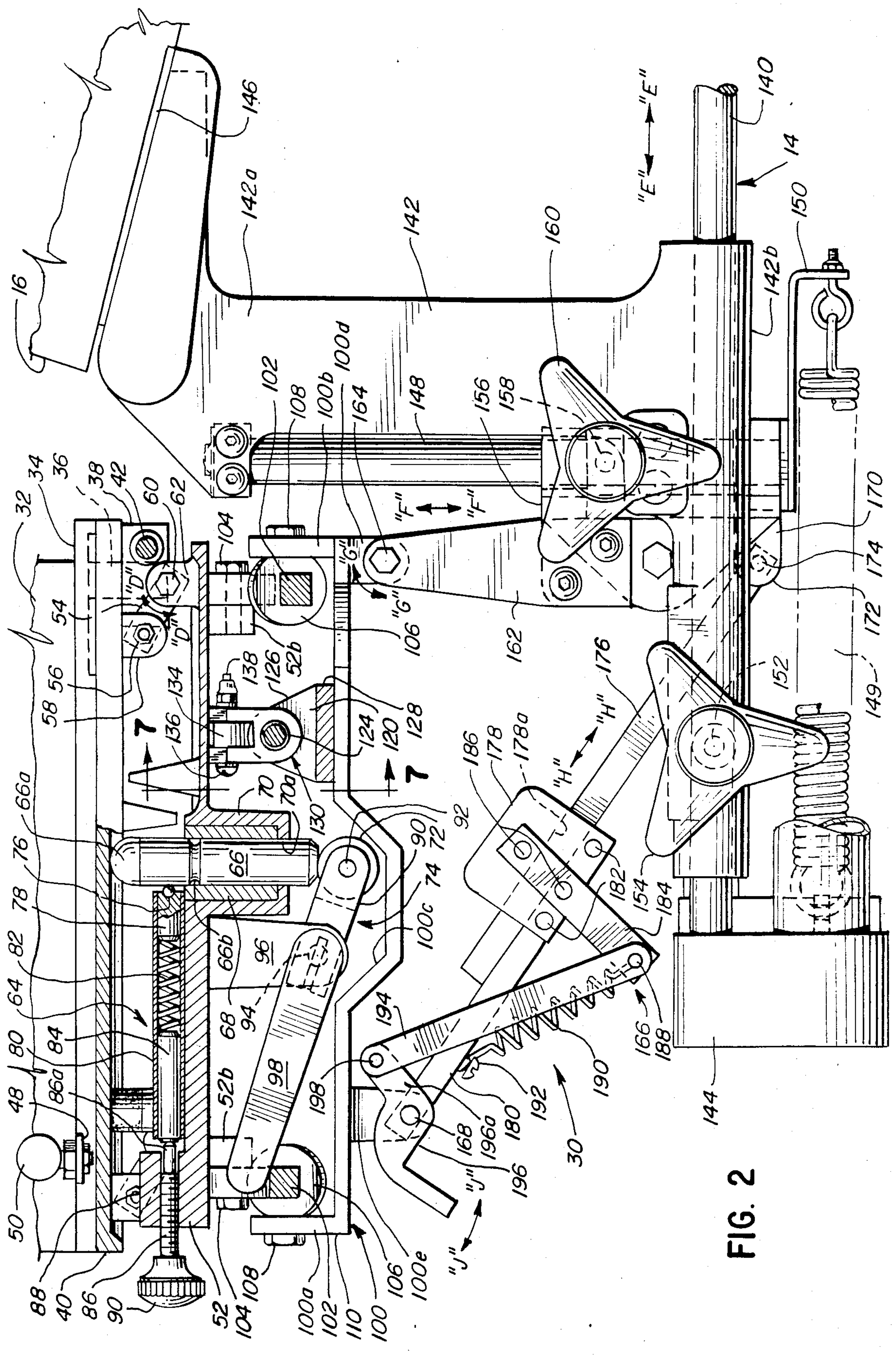
FIG. 2 is a side elevational view with portions cut away and in section of a new and improved adjustable head support for the table constructed in accordance with the features of the present invention.
Figure 8:
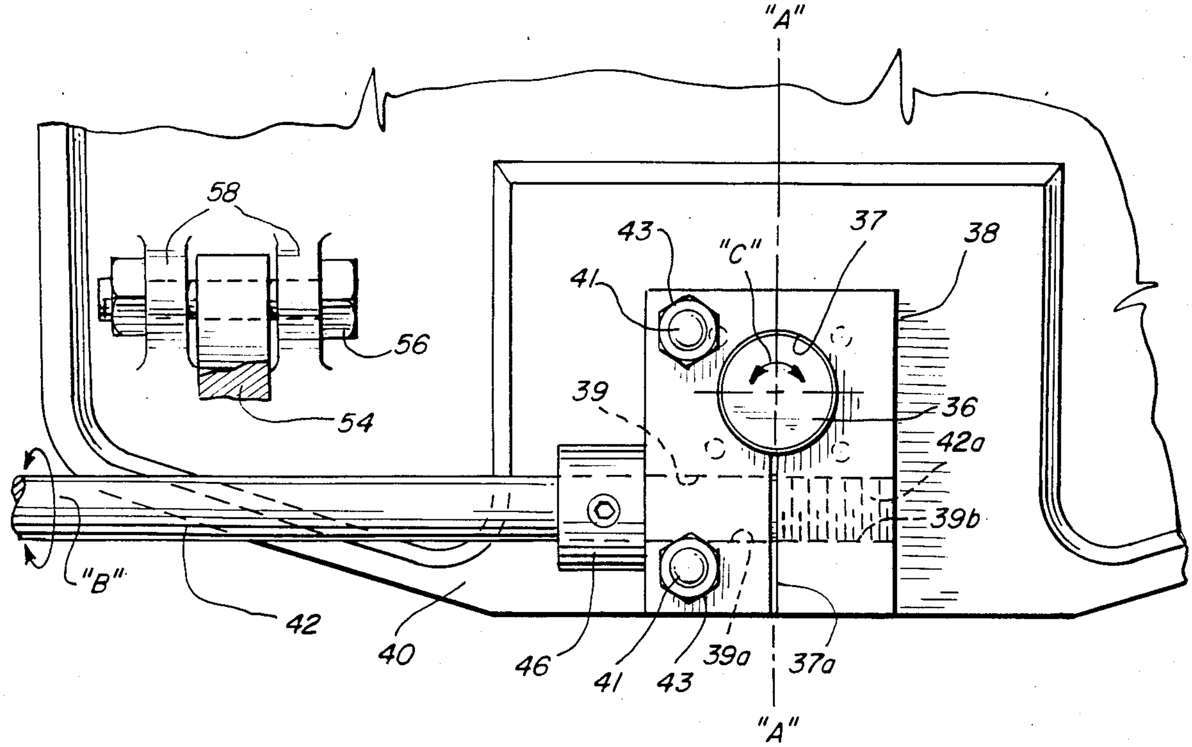
FIG. 8 is a fragmentary, bottom side elevational view of the head support apparatus looking upwardly in the direction of arrows 8—8 of FIG. 4.

The U-shaped head cushion 32 is mounted on an upper cushion plate 34 of generally rectangular shape and the cushion plate is provided with a downwardly depending, flanged pivot pin 36 (FIG. 8) adjacent the interior end of the plate. The depending pivot pin extends into an aperture 37 provided in a clamping block 38 secured to the underside of a support plate 40 as best shown in FIGS. 2, 4 and 8. The clamping block 38 is secured to the support plate by a pair of cap screws 41 and nuts 43 and is provided with a slot 37*a* extending diametrically outward of the cylindrical aperture 37 along a longitudinal axis A—A of the adjustable head support assembly 30 as shown in FIGS. 1, 4 and 8. The clamping block is provided with a segmented bore 39 transverse to the slot 37*a* having a cylindrical segment 39*a* in one half of the clamping block and a coaxial threaded segment 39*b* in the other half of the clamping block in order to threadedly receive an inner end portion 42*a* of an elongated shaft 42. A control knob 44 is mounted at the outer end of the shaft for tightening and loosening the clamping block 38 by rotation in opposite directions as illustrated by the arrow "B" of FIG. 4. A shaft collar 46 is secured to the shaft adjacent an outer edge of the clamping block so that rotation of the shaft in a clockwise direction with the knob 44 tightens the clamping block on the pivot pin and rotation of the knob in a counterclockwise direction loosens the clamping block to permit free rotation of the pivot pin within the aperture 37 so that the cushion plate 34 may be angularly adjusted relative to the longitudinal axis A—A as desired.

As shown in FIG. 4, the head cushion support plate 34 and head cushion 32 thereon can be pivoted relative to the longitudinal axis A—A of the patient table so that a patient's neck, back and head can be angularly displaced relative to lower portions of the patient's spinal column. Movement in opposite directions from a neutral position aligned with the axis A—A is facilitated by a pair of outwardly extending arms 48 having knobs 50 adjacent the outer end. When a doctor desires to displace the head cushion 32 out of alignment with respect to the longitudinal table axis A—A, the hand wheel or control knob 44 is loosened to release the tight grip of the clamping block 38 on the pin 36. The control arms 48 and knobs 50 are grasped to rotate the cushion plate 34 a desired amount in a desired direction as indicated by the arrows 'C' in FIGS. 4 and 8. If desired, suitable indicia 49 may be provided on arms 48 for calibration purposes. Once a desired angular displacement is selected, the knob 44 is tightened by clockwise rotation and the clamping block 38 secures the pin 36 so that the head cushion 32 remains in the selected position. It will thus be seen that the adjustable head support assembly 30 provides convenient means for angular displacement of the longitudinal axis of the head cushion 32 relative to the axis A—A of the table frame 14. Angular adjustment of the cushion 32 is easily accomplished by first loosening the knob 44 and then manipulating the lever 48 and knob 50 on either side of the table to pivot the support plate 40 on the axis of the pin 36 until the desired position is achieved. The knob 44 is then tightened to secure the clamping block 38 tightly around pin 36 and lock the selected adjustment in place.

The support plate 40 is interconnected to move toward and away from a lower platen 52 of generally rectangular shape by means of a plurality of short pivot links 54 located adjacent corner portions of the support plate and platen. Upper ends of the pivot links are provided with apertures for receiving pivot pins 56 comprising a cap screw and nut which project through apertures formed in pairs of spaced apart, downwardly depending, brackets 58 integrally formed on the underside of the support plate 40. Lower ends of the pivot links 54 are provided with apertures for receiving pivot pins 60 comprising cap screws and nuts which project through apertures provided in spaced apart pairs of upstanding brackets or lugs 62 provided on the upper side of the platen 52 adjacent the corner portions thereof.

Figure 5:
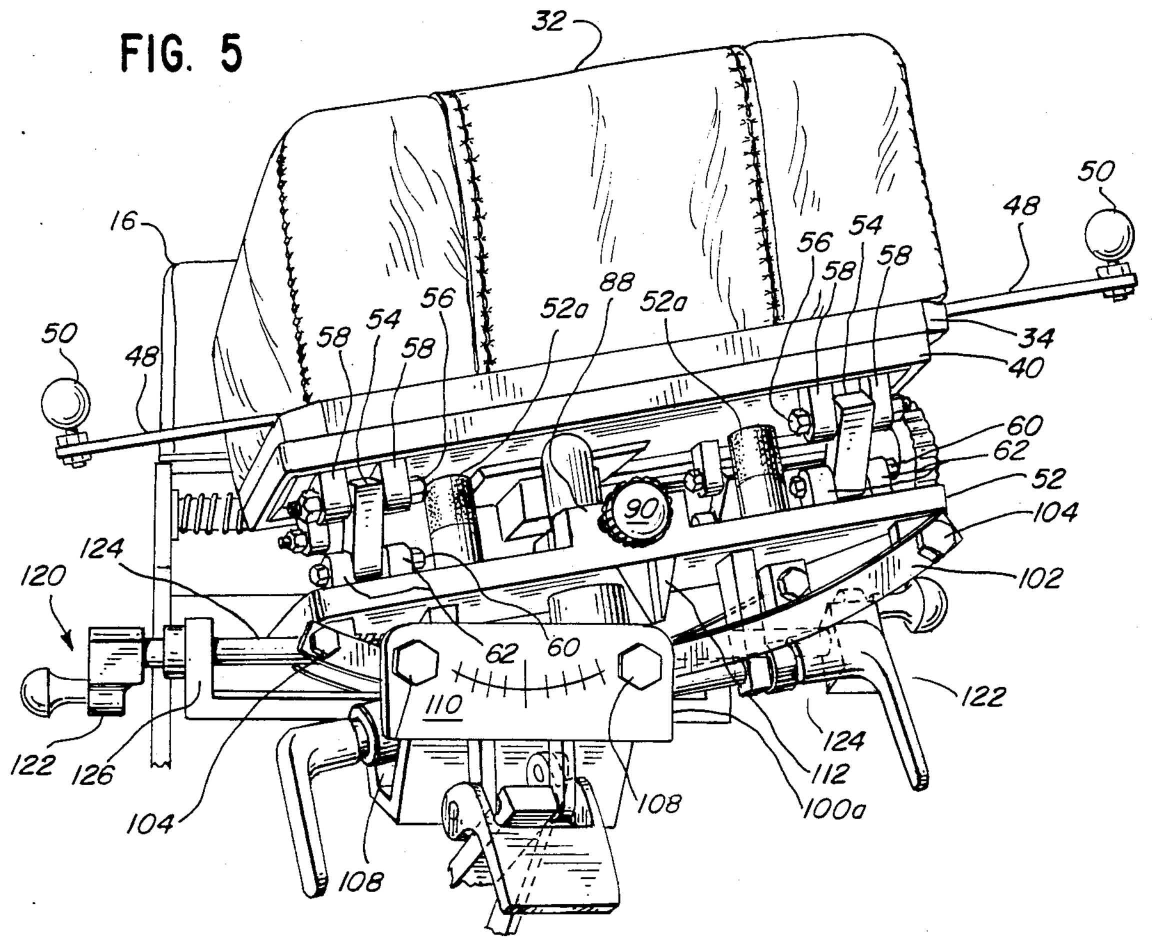
FIG. 5 is an outer end elevational view of the head support apparatus shown in an angularly displaced position.

As best illustrated in FIGS. 2 and 5, the pivot links 54 are adapted to pivot (arrow "D" FIG. 2), between the support plate 40 and the platen 52 to permit relative movement of the upper plate toward and away from the platen between a lower position as shown and an upper position at a hgiher level. Similarly, the pivot links permit return of the upper plate to the lower position when the cushion drop release is actuated as will be described hereinafter.

The foregoing interconnecting arrangement between the support plate 40 and the platen 52 accomodates a cushion drop release function of the general type as described in the aforementioned U.S. Pat. No. 4,523,581. Downward travel of the support plate towards the platen 52 is limited by a plurality of resilient stops 52*a* on the platen 52 (FIG. 5).

In accordance with the present invention, a cushion drop release mechanism 64 includes a centrally positioned support post 66 having a hemispherically shaped upper surface or head 66*a* engaging the underside of the upper support plate 40. The support post 66 is mounted for vertical reciprocal movement within a bearing sleeve 68 carried in a well 70 integrally formed in the lower platen 52 adjacent the central portion thereof. The well has an annular bottom wall provided with a central aperture 70*a* in order that the lower end portion of the support post can extend downwardly past the bottom wall for engagement with a roller 72 of a cocking assembly 74 adapted to recock the cushion drop release assembly after activation (FIG. 2).

The support post 66 is provided with an annular, detent groove 66*b* intermediate the ends for accommodating a cylindrically shaped detent 76 mounted in the end of a plunger 78 which is slidably disposed in a sleeve 80 extending along the longitudinal central axis of the platen 52 on the upper surface thereof. A bias spring 82 is mounted in the sleeve between the plunger 78 and an outer plunger 84 which is slidably positioned within the sleeve to vary the amount of compression on the bias spring when the detent 76 is seated in the support post groove 66*b*.

The position of the outer plunger 84 within the sleeve 80 and consequently the amount of resilient biasing force exerted by the spring 82 on the detent 76 is controlled by a threaded shaft 86 in coaxial alignment with the sleeve 80 and having a cylindrical inner end portion 86*a* adapted to engage the outer end surface of the outer plunger 84. The threaded shaft 86 is mounted in a threaded bore formed in an upstanding, centrally positioned lug or boss 88 integrally formed on the upper surface of the platen 52. A control knob 90 is mounted on the outer end of the threaded shaft 86 and is rotatable to move the plunger 84 inwardly or outwardly in the boss to compress the spring 82 more tightly or to permit the spring to exert a reduced level of biasing force on the inner plunger 78. It will be seen that the amount of force required to disengage the detent 76 from seated position in the groove 66*b* of the support post by the application downward pressure on the support plate 40 is selectively controllable by the control knob 90 which can effect an increase or decrease of force exerted by the biasing spring 82 on the detent.

Once the detent is forced outwardly from seated engagement within the groove 66*b*, the upper support plate 40 and head cushion 32 can drop rapidly downwardly toward the platen 52 until the respective stops 52*a* are engaged. This quick release of the support for the head cushion 32 facilitates the making of certain chiropractic adjustments to the cervical vertabrae.

After the cushion drop release assembly 64 has been activated to effect a rapid head cushion drop, the cocking assembly 74 is activated to return the support plate 40 upwardly until the detent 76 is again seated within the annualar groove 66*b* provided in the central support post 66. The cocking assembly 74 includes a bifurcated arm 90 having a support axle 92 adjacent the outer free end for supporting the roll 72 between spaced fingers of the arm. At the opposite end, the arm 90 is secured to a central portion of an axle 94, which axle in turn is journaled in bearing apertures provided in a pair of downwardly depending brackets 96 projecting downwardly from the underside of the platen 52, as shown in FIG. 2. The shaft 94 projects outwardly on opposite sides of the platen 52 and cocking levers 98 are mounted on opposite end portions of the shaft. Counterclockwise pivotal movement of the cocking lever as shown in FIG. 2 results in upward elevation of the support post 66 to reseat the detent 76 in the annular groove 66*b*. A cocking lever is provided on each side of the adjustable head support assembly 30 for convenience in operation of the cushion drop release assembly and resetting the detent 76 in the groove 66*b* of the support post 66.

In accordance with an important feature of the present invention, the platen 52 (and components supported thereby) is interconnected to pivot about a longitudinal axis which is generally parallel of the elongated axis A—A of the table frame 14 and spaced above the upper surface of the head cushion 32 to lie approximately in alignment with the axis of the vertabrae or spinal column of the patient resting on the table cushions. The platen is supported from a lower base 100 having upstanding flanges 100*a* and 100*b* at opposite ends and a trapezoidal-shaped depression 100*c* in a mid-portion for accommodating the cushion drop release and cocking assembly 74 of the cusion drop release mechanism 64 as best shown in FIG. 2. Pivotal interconnection between the platen 52 and the lower support base 100 is provided by a pair of arcuately curved arms 102 adjacent the head and neck ends of the platen and base. Each arm 102 is supported adjacent an outer end on a cap screw or pin 104 projecting through an aperture in the arm and threadedly engaged in a threaded bore provided in a depending lug or bracket 52*b* formed on the underside of the platen 52 as best shown in FIG. 2. The lugs 52*b* are positioned adjacent corner portions of the platen and are drilled and tapped to receive the threaded end portions of the cap screws 104.

The curved arms 102 curve downwardly from opposite ends and are formed with a radius of curvature such that the center or origin of the curve is spaced above the head cushion 32 at approximately the same level as the spinal column of a patient laying on the cushions of the table. Rotational adjustment of a patients vertabrae can be achieved by angularly displacing the platen 52 to either side of a neutral position directly below the axis A—A (FIG. 4). Each curved arm 102 is supported for longitudinal sliding movement within curved bores of a pair of bearing assemblies 106 which are secured to opposite end portions of the respective base end flanges 100*a* and 100*b*. Cap screws or other fasteners 108 are provided for securing the bearing assemblies in place on the end flanges.

Figure 3:
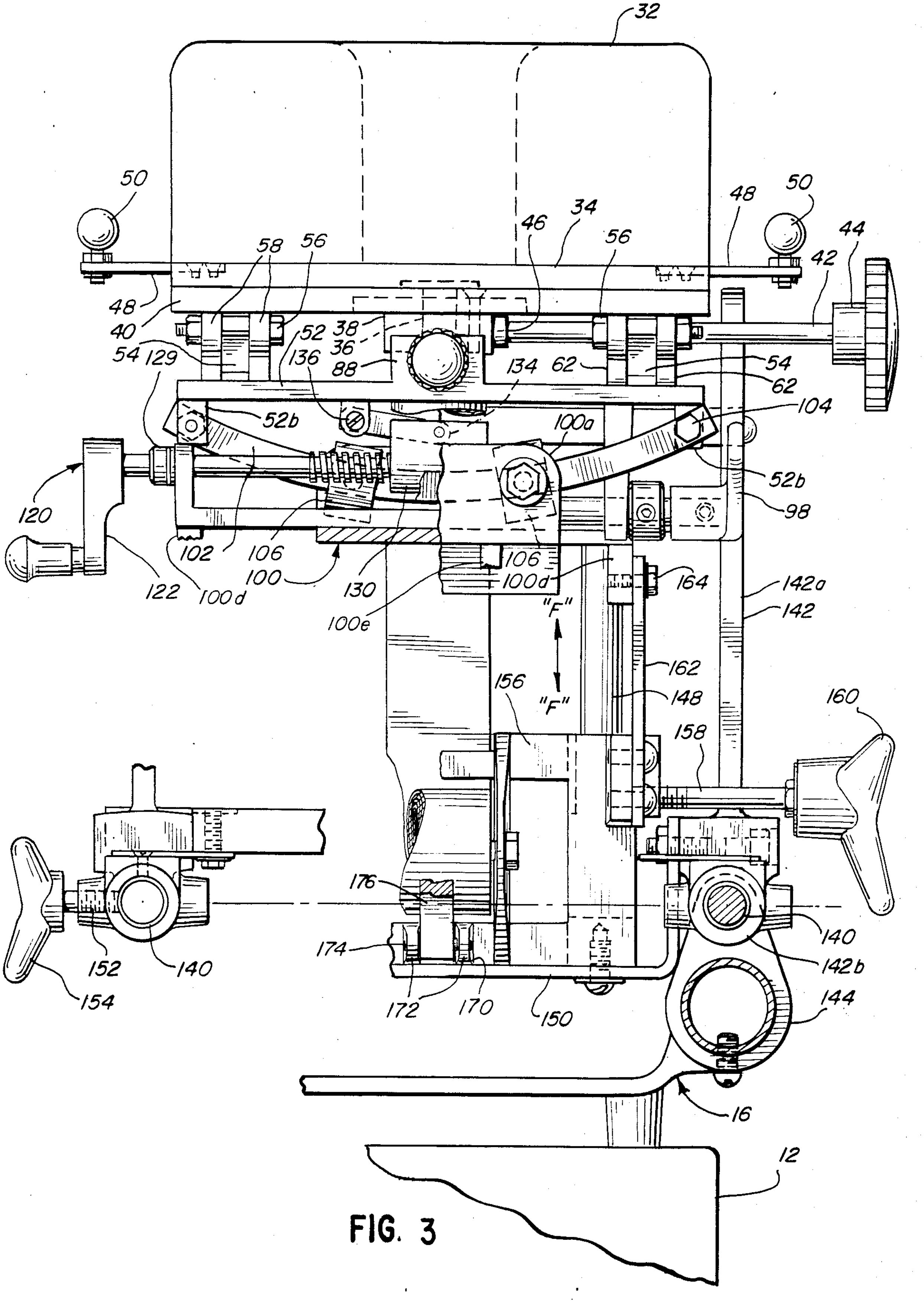
FIG. 3 is a transverse cross sectional view of the adjustable head support with portions cut away and in section.
Figure 6:
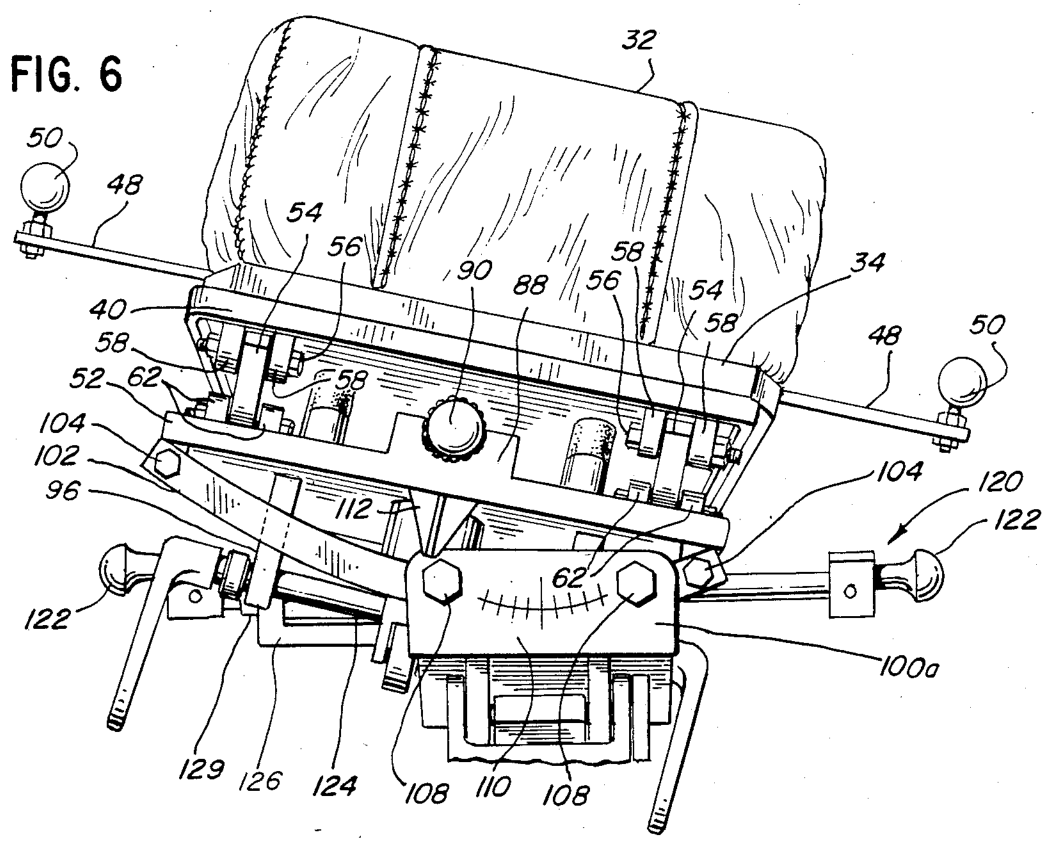
FIG. 6 is an outer end elevational view of the head support similar to FIG. 5 but shown in another angular displaced position in an opposite direction.

Referring now to FIGS. 3, 5, 6 and 7, the platen is movable from a center or neutral position as shown in FIG. 3 to a angularly displaced position (as shown in FIGS. 5 and 6) wherein the head cushion 32 is tilted about a longitudinal axis extending above the head cushion 32 and generally aligned with the elongated axis A—A of the patient table frame 14 (FIG. 1). As illustrated in FIGS. 5 and 6, tilting of the head cushion can be in either direction relative to a true horizontal position as shown in FIG. 3 in order to accommodate the needs of various patients. In addition, the amount of angular tilt can be selectively controlled and for this purpose, a scale plate 110 with angular gradations is secured to the base flange 100*a* by means of the cap screws 108. A tilt pointer 112 is mounted on the outer end of the platen 52 to register with the arcuate scale of the scale plate 110 so that precise angular displacement can be selected. When a central line of the pointer 112 is centered with a vertical grading mark on the scale plate 110, the head cushion 32 is in a neutral position (generally horizontal) with respect to the longitudinal axis "A"—"A" of the table.

In order to select and control the amount of angular displacement as desired, the adjustable head support assembly 30 is provided with a crank assembly 120 best shown in FIGS. 5, 6 and 7, which employs a pair of hand cranks 122 on opposite sides of the head cushion 32 for convenient operation from either side of the table. The hand cranks 122 are mounted on opposite, outer end portions of a threaded shaft 124 supported for rotation in a pair of upstanding brackets 126 provided at opposite ends of a cross piece 128 secured to the support base 100. The shaft 124 is limited against longitudinal displacement relative to the brackets 126 by annular collars 129 held in place on the shaft by appropriate fasteners such as set screws. The shaft 124 is provided with a threaded segment 124*a* intermediate its ends and this threaded segment is engaged within a threaded, internal bore of a traveling nut 130 designed to move longitudinally of the shaft from a central position or neutral position (solid lines FIG. 7) to a displaced position to the right or left (as shown in dotted lines) for tilting the platen 52 to provide angular displacement of the head cushion 32.

The traveler nut 130 is pivotally interconnected to a lug 132 depending downwardly from the underside of the platen 52 by a pivot link 134 and pivot pins or cap screws 136 and 138 are provided at opposite ends of the link for pivot connection to the lug and traveler nut, respectively. Rotation of either hand crank 122 of the hand crank assembly 120 permits a doctor to easily control and select the precise amount of angular displacement between the head supporting cushion 32 and the adjacent cushions 16, 18 and 20, etc. on the table frame 14. Rotational displacement of the cushion 32 takes place around an axis spaced above the cushion generally aligned with the spinal column or neck of the patient laying on the table because of the unique support arrangement interconnecting the platen 52 and lower support base 100 as described. The scale plate 110 and pointer 112 provide a convenient indicator for use in selecting the desired abount of angular displacement.

In accordance with another feature of the present invention the adjustable head support assembly 30 includes structure for adjustably supporting the base 100 to provide for elevational adjustment between the head cushion 32 and the adjacent cushion 16 as well as adjustment of the space between these cushions and adjustment of the angular disposition of the upper surfaces thereof. The cushion 16 is supported from a pair of upstanding brackets 142 which are mounted for sliding movement as indicated by the arrows "E—E" on elongated rod like elements 140 of the frame 14 at the head end of the table the rod like elements are interconnected by an end piece 144 secured to the rods 140. Each side frame bracket 140 includes an upstanding portion 142*a* and a hollow tubular sleeve 142*b* mounted for adjustable sliding movement on a rod 140 of the frame. A cross member 146 is provided to connect upper end portions of the bracket legs 142*a* and the table cushion 16 is secured above the cross member 146 as shown in FIG. 2. Each bracket 142 also includes an upstanding rod like element 148 extending upwardly and spaced inwardly of the side frame leg 142*a*. The sleeve 142*b* of each side bracket 142 is biased towards the end frame member 144 by a coil spring 149 interconnected between the end frame member 144 and a lower cross member 150 as shown in FIGS. 2 and 3.

The position of the sleeves 142*b* on the rods 140 may be adjustably selected by movement in the direction of the arrows "E—E" and when a desired position is obtained the side frame members are secured by means of a threaded shaft 152 having a star shaped control knob or handle 154 at the outer end for tightening or loosening as desired to move or set the position of the side frame members 142 on the rods 140 of the table frame 14. Similarly, a threaded shaft and control handle 154 is provided on the opposite side member so that the structure can be rigidly secured in place from both sides. Each rod 148 provides a supporting guideway for a sleeve member 156 slideably disposed thereon for movement upwardly and downwardly as indicated by the arrows "F—F" (FIG. 2) to select the appropriate level between the head cushion 32 and the adjacent cushion 16. Once the desired elevation of the sleeves 156 is selected the position is secured by means of inwardly extending threaded shafts 158 with control handles of star or triangular shape 160 as shown. Each sleeve 156 provides support for an upstanding leg 162 having an aperture adjacent the upper end to receive a cap screw 164 which is threadedly engaged in an aperture provided in a depending lug 100*d* provided on the bottom of the support base 100 at the corner thereof as shown best in FIGS. 2 and 3. Cap screws 164 act as pivot axles so that the support base 100 of the head piece assembly 30 can pivot as indicated by the arrow "G—G" FIG. 2 to provide a range of different angular relations between the head cushion 32 and cushion 16.

In order to permit pivotal movement of the support plate 100 about the axis of the cap screws 164 to selectively control the angular relationship between the head cushion 32 and the cushion 16 the adjustable head support assembly 32 of the present invention includes an adjustable linkage mechanism generally referred to by the numeral 166 (FIG. 2) pivotally connected between an upper pivot axle 168 supported by a pair of depending lugs 100*e* on the base 100 adjacent the outer end on the underside thereof. The lower end of the linkage assembly 166 is pivotally interconnected to a centrally positioned base 170 secured to the lower cross member 150. The base 170 is provided with a pair of outwardly extending ears or lugs 172 having apertures therein for receiving a pivot pin 174 which extends through an aperture provided in a lower end of an elongated lower linkage member 176 of the assembly 166. An upper portion of the lower member 176 is slidably disposed within a slot 178*a* formed in a block like element 178 of U-shaped transverse cross section. The lower surface of the slot is closed by the upper surface of an upper link 180 having an upper end connected to the upper pivot axle 168. The lower end portion of the upper link is secured to the block by appropriate fasteners 182 and the lower link is slidable within the slot 178*a* of the box as indicated by the arrow "H—H".

Normally the block 178 is biased in a clockwise direction as shown in FIG. 2 relative to the lower link member 176 to preclude relative sliding adjustment between the upper and lower link members. This biasing arrangement is accomplished by a pivot arm 184 fastened to the block with suitable fasteners 186 on opposite sides of the slot 178*a*. A pin 188 is provided at the lower end of the arm 184 and a bias spring 190 is connected to the pin at a lower end. An upper end of the bias spring is connected to the upper link 180 by a cap screw or other fastener 192 so that the spring exerts a counter clockwise bias on the block 178 at the lower end of the upper link relative to the lower link 176.

In order to permit relative adjustment between the upper and lower links 180 and 176 respectively the biasing spring 190 is extended by means of a link 194 connected at its lower end to the pivot pin 188 and at an upper end to a toe portion 196*a* of a release lever 196. The release lever and link 194 are interconnected by a suitable pin 198 in order to release the clamping effect of the block 178 on the lower link 176 so that relative adjustment of the upper and lower links in the direction of the arrows "H—H" can be made to provide pivotal movement about the cap screws 164 (arrows G) for the head assembly as a whole. The annular release member 196 is pivoted in a clockwise direction as indicated by the arrow J (FIG. 2) about the pivot axis 168 to overcome the biasing force of the spring 190 and permit the lower link 176 to slide up or down within the slot 178*a* in the block. Release of manual pressure on the member 196 permits the spring 190 to again secure the link members 176 and 180 against relative longitudinal adjustment to support the base of the adjustable head support assembly in a selected pivotal position. From the foregoing it will be seen that the head cushion 32 is movable up and down relative to the cushion 16 and is pivotal relative thereto to increase or decrease the spacings between the cushions and provide a selected range of angular adjustments between the upper surfaces of the respective cushions as desired.

Although the present invention has been described with reference to a single illustrated embodiment thereof, it should be understood that numerous other modifications and embodiments can be made by those skilled in the art that will fall within the spirit and scope of the principles of this invention.

What is claimed as new and is desired to be secured by Letters Patent is:

1. Adjustable support apparatus for a chiropractic table cushion, comprising:

a lower base;

a platen spaced above said base for supporting said cushion;

interconnecting means between said base and said platen supporting said platen for angular displacement relative to said base about an axis extending longitudinally thereof and spaced above said platen; and adjustment control means for selectively controlling the amount of angular displacement between said platen and said base, said control means being operable to angularly displace said platen in opposite directions from a neutral position generally parallel of said base and including threaded shaft means supported for rotational movement and restricted against longitudinal movement on one of said platen and said base, and traveler means threadedly engaged with said shaft means for relative longitudinal movement therein in response to selected rotation of said shaft means and connected to move the other of said base and platen.

2. The adjustable support apparatus of claim 1, including:

a support plate mounted above said platen; and second interconnecting means between platen and support plate for supporting said plate for movement toward and away from said platen, said second interconnecting means including releasable detent means for supporting said support plate in a first position elevated above said platen and releasable to permit said support plate to drop to a second lower position relative to said platen.

3. The adjustable support apparatus of claim 2, including:

an upper cushion plate for supporting a table cushion for patient resting on said table mounted above said support plate for relative pivotal movement about an upstanding axis normal thereto.

4. The adjustable support apparatus of claim 3 including clamping means for releasably securing said upper cushion plate in a selected relative rotational position on said support plate.

5. The adjustable support apparatus of claim 1 wherein;

said interconnecting means includes at least one arcuate track mounted for longitudinal movement between opposite ends of said track and supported in a support sleeve to provide for said relative angular displacement between said base and said platen.

6. The adjustable support apparatus of claim 5 wherein said arcuate track extends transversely of said longitudinal axis and depends below said platen, and wherein said support sleeve is fixed relative to said base.

7. The adjustable support apparatus of claim 6 including a pair of said arcuate tracks adjacent opposite ends of said platen and a pair of said support sleeves therefor at opposite ends of said base.

8. The adjustable support apparatus of claim 7 wherein said adjustment control means is engaged between said base and platen intermediate said tracks.

9. The adjustable support apparatus of claim 8 wherein said adjustment control means includes rotatable shaft means extending transversely of said platen and base having opposite end portions accessible from opposite sides of said palten and base for selective rotation thereof.

10. The adjustable suport apparatus of claim 9 including hand crank means on at least one of said opposite end portions of said shaft means for facilitating rotation thereof.

11. The adjustment support apparatus of claim 10 incldiung bearing means for supporting said shaft means for rotation while restraining longitudinal movement relative to one of said base and platen and traveler means mounted for longitudinal movement on said shaft means upon rotation thereof and connected to the other of said base and platen.

12. The adjustment support apparatus of claim 11 including indicator means for providing an indication of the relative angular position between said base and said platen.

13. Adjustable support apparatus for a chiropractic table, comprising:

a lower base;

aplaten spaced above said base;

interconnecting means between said base and said platen supporting said platen for angular displacement relative to said base about an axis extending longitudinally thereof and spaced above said platen, said interconnecting means including a pair of arcuate tracks mounted for longitudinal movement between opposite ends of said tracks and supported in respective support sleeves to provide for said relative angular displacement between said base and said platen, said respective tracks being positioned adjacent opposite ends of said platen, extending transversely of said longitudinal axis and depending below said platen, said support sleeves being fixed relative to opposite ends of said base; and adjustment control means for selectively controlling the amount of angular displacement between said platen and said base, said control means being operable to angularly displace said platen in opposite directions from a neutral position generally parallel of said base, said adjustment control means engaged between said base and said platen intermediate said tracks and including rotatable shaft means extending transversely of said platen and said base having opposite end portions accessible from opposite sides of said platen and base for selective rotation thereof.

14. The adjustable support apparatus of claim 13 including a hand crank means on at least one of said opposite end portions of said shaft means for facilitating rotation thereof.

15. The adjustment support apparatus of claim 13 including bearing means for supporting said shaft means for rotation while restraining longitudinal movement relative to one of said base and platen and traveler means mounted for longitudinal movement on said shaft means upon rotation thereof and connected to other of said base and platen.

16. The adjustment support apparatus of claim 15 including indicator means for providing an indication of the relative angular position between said base and said platen.

* * * * *